United States Patent
Yan et al.

(10) Patent No.: US 12,091,731 B2
(45) Date of Patent: Sep. 17, 2024

(54) BIOMEDICAL BETA TITANIUM ALLOY AND PREPARATION METHOD THEREOF

(71) Applicant: Institute of New Materials, Guangdong Academy of Sciences, Guangdong (CN)

(72) Inventors: Xingchen Yan, Guangdong (CN); Cheng Chang, Guangdong (CN); Qingkun Chu, Guangdong (CN); Changguang Deng, Guangdong (CN); Min Liu, Guangdong (CN)

(73) Assignee: Institute of New Materials, Guangdong Academy of Sciences, Guangzhou (CN)

( * ) Notice: Subject to any disclaimer, the term of this patent is extended or adjusted under 35 U.S.C. 154(b) by 0 days.

(21) Appl. No.: 17/874,266

(22) Filed: Jul. 26, 2022

(65) Prior Publication Data

US 2023/0023628 A1    Jan. 26, 2023

(30) Foreign Application Priority Data

Jul. 26, 2021 (CN) .......................... 202110848180.9

(51) Int. Cl.
*C22C 14/00* (2006.01)
*B22F 1/05* (2022.01)
(Continued)

(52) U.S. Cl.
CPC ................ *C22C 14/00* (2013.01); *B22F 1/05* (2022.01); *B22F 1/065* (2022.01); *B22F 9/14* (2013.01);
(Continued)

(58) Field of Classification Search
CPC ......... C22C 1/0458; C22C 14/00; B22F 1/05; B22F 1/065; B22F 9/14; B22F 2301/205;
(Continued)

(56) References Cited

U.S. PATENT DOCUMENTS

| 4,857,269 A * | 8/1989 | Wang ...................... C22C 14/00 |
| | | 36/152 |
| 2022/0025488 A1* | 1/2022 | Alabort Martinez ... C22F 1/183 |

FOREIGN PATENT DOCUMENTS

| CN | 105618775 A | * | 6/2016 |
| CN | 111235429 A |   | 6/2020 |
| CN | 112222409 A | * | 1/2021 ............. A61L 27/06 |

OTHER PUBLICATIONS

Duan R.; et al.; "A high strength and low modulus metastable B Ti-12Mo-6Zr-2Fe Alloy fabricated by laser powder bed fusion"; J. of Additive Manufacturing; 37, 2021, Available online Nov. 14, 2020 (Year: 2020).*

(Continued)

*Primary Examiner* — Alexandra M Moore
*Assistant Examiner* — Austin Pollock (57) ABSTRACT

Disclosed is a biomedical β titanium alloy and a preparation method thereof. Its composition includes: Mo: 9.20-13.50%; Fe: 1.00-3.20%; Zr: 3.50-8.20%; Ta: 0-1.00%; the balance is Ti. The β titanium alloy is suitable for the laser additive manufacturing technology, and the prepared parts have a dense equiaxed grain structure with ultra-low grain size and a small number of columnar grain structures, which produces a fine-grain strengthening effect, and greatly improve the hardness and tribocorrosion performance of the alloy material. Also provided is a method for preparing a non-toxic, low-elasticity, and tribocorrosion resistant biomedical β titanium alloy material. A powder prepared from the above alloy components is subjected to a laser additive manufacturing technology to prepare a corresponding β titanium alloy with high-hardness, good tribocorrosion resistance and extremely low cytotoxicity. Moreover, the prepared material has good weldability and is a special metal alloy powder suitable for laser additive manufacturing.

5 Claims, 6 Drawing Sheets

(51) Int. Cl.
*B22F 1/065* (2022.01)
*B22F 9/14* (2006.01)
*C22C 1/04* (2023.01)

(52) U.S. Cl.
CPC ...... *C22C 1/0458* (2013.01); *B22F 2301/205* (2013.01); *B22F 2304/10* (2013.01)

(58) Field of Classification Search
CPC ...... B22F 2304/10; B22F 10/20; B22F 10/22; B22F 10/25; B22F 10/28
See application file for complete search history.

(56) References Cited

OTHER PUBLICATIONS

P. Mohan et al., Effect of Fe content, sintering temperature and powder processing on the microstructure, fracture and mechanical behaviours of Ti-Mo-Zr-Fe alloys, Journal of Alloys and Compounds, Sep. 25, 2017, pp. 1215-1225, vol. 729, also available at https://doi.org/10.1016/j.jallcom.2017.09.255.

* cited by examiner

BIOMEDICAL BETA TITANIUM ALLOY AND PREPARATION METHOD THEREOF

CROSS REFERENCE TO RELATED APPLICATION

The present application claims priority from Chinese Patent Application No. 202110848180.9 filed on Jul. 26, 2021, the contents of which are incorporated herein by reference in their entirety.

TECHNICAL FIELD

The invention relates to the technical field of metal materials, in particular to a biomedical β titanium alloy and a preparation method thereof.

BACKGROUND

Medical titanium alloy has good biocompatibility and is currently the preferred material for medical implants. In recent years, metal 3D printing based on digital optical image acquisition and personalized tissue repair technology have sparked a new research boom in medical titanium alloys. However, the commonly used medical titanium alloy implant (Ti6Al4V ELI) at present is very different from human bone tissue in elastic modulus, and there are toxic ions released after long-term implantation, which prevent the benign combination of titanium alloy and bone tissue, and limit the long-term safety during the service life. Therefore, development of new titanium alloys that are more suitable for human bone implantation has become the focus and hot trend of current research and development.

β-Ti alloy has the characteristics of no toxic elements, high strength and low elastic modulus. Designing and developing β-Ti alloys with lower modulus and better comprehensive properties has become the development focus and research hot topic of medical titanium alloy materials at home and abroad. However, due to the discrepancy among the creature bones and the randomness of the shape of the defect sites, it is difficult for the standardized implants manufactured by traditional processing methods to meet the actual clinical needs. Therefore, personalized repair of clinical bone defect carried out by metal 3D printing technology has gradually become an effective method for the treatment of orthopedic diseases. But so far, there are no report of commercialized medical β-Ti alloy metal 3D printing powders and related products.

Metal 3D printing can realize the perfect combination of 3D personalized design, pore structure customization and rapid net shaping of metal implants, and has become the key development direction and future development trend of high-end personalized medical device design, manufacturing, application and promotion. However, selection and design of metal 3D printing β-Ti functional material system, controllable fabrication of personalized medical multifunctional materials, surface interface research of bone tissue biomaterials, systematic clinical verification and customized response are still lack of research and development (R&D) that need to be overcome urgently.

SUMMARY OF THE INVENTION

The object of the present disclosure is to overcome the shortcomings of the prior art and provide a biomedical β titanium alloy and a preparation method thereof.

To achieve the above object, the technical scheme adopted in the present disclosure is as follows:

In a first aspect, the present disclosure provides a biomedical β titanium alloy, the β titanium alloy comprises the following components by mass percentage: Mo: 9.2-13.5%; Fe: 1-3.2%; Zr: 3.5-8.2%; Ta: 0-1%; the balance are Ti and inevitable impurities.

According to the research of the inventor, Mo, Ta and Fe elements can lower the β transition temperature, be infinitely dissolved in the β phase, and expand the β phase region. Among them, Fe element is one of the strongest β-phase stabilizing elements, and Mo element has the effect of improving the thermal stability of chromium and iron alloys. The biomedical β titanium alloy of the present disclosure is a non-toxic, low-elastic, tribocorrosion resistant, high-performance material that can be used for metal additive manufacturing.

Further, the β titanium alloy has a particle size of 10-75 μm.

In a second aspect, the present disclosure provides a method for manufacturing the above-mentioned biomedical β titanium alloy, comprising the following steps:

(1) Mixing Mo, Fe, Zr, Ta and Ti according to the mass percentages, and smelting and forging into a rod;
(2) Preparing a power from the rod obtained in step (1) by a plasma rotating electrode process, and collecting an alloy powder with a particle size of 12-75 μm;
(3) Vacuum drying the alloy powder collected in step (2) to obtain a β titanium alloy.

Based on the research of the inventor, the β titanium alloy prepared by the preparation method of the present disclosure has excellent fluidity, high purity and weldability.

Further, in step (1), the rod has a diameter of 15-30 mm, and a length of 10-150 mm.

Further, in step (1), the rod has a diameter of 15-20 mm, and a length of 20-30 mm.

Further, the plasma rotating electrode process in step (2) comprises the following steps: heating the rod in step (1) to 1500-1750° C. and smelting for 60-80 min to obtain a molten alloy; and subjecting the molten alloy to fluidized bed spray granulation under high-purity argon gas.

Further, process parameters of the fluidized bed spray granulation are listed as follows: firstly, vacuum a working chamber for the process; and a vacuum degree of a atomizing chamber reaches $5\times10^{-3}$ Pa or more, and then high-purity argon gas is introduced to make the pressure in the atomizing chamber reach 0.04-0.08 MPa; a plasma gun is set to have a power of 200 kW, a rotation speed is 15000-18000 r/min, and a spherical powder is formed after cooling under the inert gas in the chamber and collected into a powder bin.

Further, in step (2), the powder is spherical, and a particle size of the collected powder is 35-50 μm.

Further, in step (3), the vacuum drying is carried out at a temperature of 120-200° C., and under a pressure of 100-200 MPa.

In a third aspect, the present disclosure also provides application of the above-mentioned biomedical β titanium alloy in medical materials. Specifically, a 3D model is established by using a 3D modeling software according to a target part, and the 3D model is imported into an additive manufacturing system to generate a scanning path of the part; the above-mentioned biomedical β titanium alloy is processed into a biomedical material by the additive manufacturing system.

The β titanium alloy described in the disclosure is suitable for the laser additive manufacturing technology, and the prepared parts have a dense equiaxed grain structure with ultra-low grain size and a small amount of columnar crystal structures, which not only plays a role in fine grain strengthening, but also has the effect on greatly improving the hardness and tribocorrosion resistance of alloy materials.

The beneficial effects of the present disclosure are:
(1) The biomedical β titanium alloy material prepared by the present disclosure basically has a single β-Ti phase composed of fine and dense equiaxed crystals and a small amount of columnar crystals after being processed and formed, which greatly improves the strength, hardness and tribocorrosion resistance of the material while ensuring the plasticity and tenacity.
(2) The biomedical β titanium alloy material prepared by the present disclosure has low oxygen content, few impurities, high alloy purity, and excellent weldability and formability.
(3) The biomedical β titanium alloy material prepared by the present disclosure does not contain toxic elements, has extremely low cytotoxicity and good cytocompatibility.

DETAILED DESCRIPTION OF ILLUSTRATED EXAMPLES

In order to better illustrate the purpose, technical solutions and advantages of the present invention, the present disclosure will be further described below with reference to specific embodiments.

Example 1

A raw material composition of a biomedical β titanium alloy is as follows by mass percentage: Mo: 11.25%; Fe: 1.75%; Zr: 5.82%; Ta: 0.21%; and the balance is Ti.

The preparation method is as follows:
(1) Weigh the raw material including Zr, Mo, Ta, Fe, Ti and a very small amount of inevitable C and Si, and the purity of each component is 99.2 wt %. After being smelted in a crucible, the raw material was forged into a rod with a diameter of 29.2 mm and a length of 150 mm for the preparation of a spherical powder.
(2) By adopting plasma rotating electrode process to prepare the powder, the rod is heated to 1700° C. in a vacuum environment, a molten alloy was obtained after smelting for 65 minutes, and high-purity argon was introduced for fluidized bed spray granulation. Collect the alloy powder with a particle size of 12-75 The key parameters of the granulation process and detailed steps are as follows: first, the working chamber was vacuumized, the vacuum degree of the atomizing chamber reached $5 \times 10^{-3}$ Pa, and then high-purity argon gas was introduced to make the pressure in the chamber reach 0.06 MPa. The power of the plasma gun was at 200 kW, the rotation speed was 16000 r/min, and a spherical powder was formed after cooling under the inert gas in the chamber and collected into the powder bin.
(3) Put the collected alloy powder into a vacuum drying box, where the vacuum pressure was about 120 MPa. Then the vacuum drying box was heated to 120° C. at a heating rate of 80° C./min and vacuum drying was performed after holding the temperature for 2 h. The titanium-based alloy powder obtained after drying is the biomedical β titanium alloy material of the present disclosure, the alloy powder was put into a vacuum bag to be evacuated and stored for later use.

Example 2

A raw material composition of a biomedical β titanium alloy is as follows by mass percentage: Mo: 9.57%; Fe: 2.35%; Zr: 7.88%; Ta: 0.46%; and the balance is Ti.

The preparation method is as follows:
(1) Weigh the raw material including Zr, Mo, Ta, Fe, Ti and a very small amount of inevitable C and Si, and the purity of each component is 99.2 wt %. After being smelted in a crucible, the raw material was forged into a rod with a diameter of 29.2 mm and a length of 150 mm for the preparation of a spherical powder.
(2) By adopting plasma rotating electrode process to prepare the powder, the rod was heated to 1600° C. in a vacuum environment, a molten alloy was obtained after smelting for 75 minutes, and high-purity argon was introduced for fluidized bed spray granulation. Collect the alloy powder with a particle size of 12-75 The key parameters of the granulation process and detailed steps are as follows: first, the working chamber was vacuumized, the vacuum degree of the atomizing chamber reached $5 \times 10^{-3}$ Pa, and then high-purity argon gas was introduced to make the pressure in the chamber reach 0.06 MPa. The power of the plasma gun was at 200 kW, the rotation speed was 16000 r/min, and spherical powder was formed after cooling under the inert gas in the chamber and collected into the powder bin.
(3) Put the collected alloy powder into a vacuum drying box, where the vacuum pressure was about 120 MPa. Then the vacuum drying box was heated to 120° C. at a heating rate of 80° C./min and vacuum drying was performed after holding the temperature for 2 h. The titanium-based alloy powder obtained after drying is the biomedical β titanium alloy material of the present disclosure, the alloy powder was put into a vacuum bag to be evacuated and stored for later use.

Example 3

A raw material composition of a biomedical β titanium alloy is as follows by mass percentage: Mo: 13.25%; Fe: 3.05%; Zr: 3.67%; Ta: 0.82%; and the balance is Ti.

The preparation method is as follows:
(1) Weigh the raw material including Zr, Mo, Ta, Fe, Ti and a very small amount of inevitable C and Si, and the purity of each component is 99.2 wt %. After being smelted in a crucible, the raw material is forged into a rod with a diameter of 29.2 mm and a length of 150 mm for the preparation of a spherical powder.
(2) By adopting plasma rotating electrode process to prepare the powder, the rod was heated to 1700° C. in a vacuum environment, a molten alloy was obtained after smelting for 65 minutes, and high-purity argon was introduced for fluidized bed spray granulation. Collect the alloy powder with a particle size of 12-75 The key parameters of the granulation process and detailed steps are as follows: first, the working chamber is vacuumized, the vacuum degree of the atomizing chamber reached $5\times10^{-3}$ Pa, and then high-purity argon gas was introduced to make the pressure in the chamber reach 0.06 MPa. The power of the plasma gun was at 200 kW, the rotation speed was 16000 r/min, and a spherical powder was formed after cooling under the inert gas in the chamber and collected into the powder bin.
(3) Put the collected alloy powder into a vacuum drying box, where the vacuum pressure was about 120 MPa. Then the vacuum drying box was heated to 120° C. at a heating rate of 80° C./min and vacuum drying was performed after holding the temperature for 2 h. The titanium-based alloy powder obtained after drying is the biomedical β titanium alloy material of the present disclosure, the alloy powder was put into a vacuum bag to be evacuated and stored for later use.

Comparative Example 1

A raw material composition of a biomedical β titanium alloy is as follows by mass percentage: Mo: 0%; Fe: 2.00%; Zr: 4.25%; Ta: 0.08%; Ti: 93.67%.
The preparation method is as follows:
(1) Weigh the raw material including Zr, Ta, Fe, Ti and a very small amount of inevitable C and Si. The purity of each component is 99.0 wt %. After being smelted in a crucible, the raw material is forged into a rod with a diameter of 30 mm and a length of 152 mm for the preparation of a spherical powder.
(2) By adopting plasma rotating electrode process to prepare the powder, the rod was heated to 1750° C. in a vacuum environment, a molten alloy was obtained after smelting for 80 minutes, and high-purity argon was introduced for fluidized bed spray granulation. Collect the alloy powder with a particle size of 12-75 The key parameters of the granulation process and detailed steps are as follows: first, the working chamber is vacuumized, the vacuum degree of the atomizing chamber reached $5\times10^{-3}$ Pa, and then high-purity argon gas was introduced to make the pressure in the chamber reach 0.06 MPa. The power of the plasma gun was at 200 kW, the rotation speed was 16000 r/min, and a spherical powder was formed after cooling under the inert gas in the chamber and collected into the powder bin.
(3) Put the collected alloy powder into a vacuum drying box, where the vacuum pressure was about 120 MPa. Then the vacuum drying box was heated to 120° C. at a heating rate of 80° C./min and vacuum drying was performed after holding the temperature for 2 h. The titanium-based alloy powder obtained after drying is the biomedical β titanium alloy material of the present example, the alloy powder was put into a vacuum bag to be evacuated and stored for later use.

Comparative Example 2

A raw material composition of a biomedical β titanium alloy is as follows by mass percentage: Mo: 10.8%; Fe: 0%; Zr: 6.38%; Ta: 0.11%; Ti: 82.71%.
The preparation method is as follows:
(1) Weigh the raw material including Zr, Ta, Mo, Ti and a very small amount of inevitable C and Si. The purity of each component is 99.0 wt %. After being smelted in a crucible, the raw material is forged into a rod with a diameter of 29 mm and a length of 150 mm for the preparation of a spherical powder.
(2) By adopting plasma rotating electrode process to prepare the powder, the rod was heated to 1700° C. in a vacuum environment, a molten alloy was obtained after smelting for 70 minutes, and high-purity argon was introduced for fluidized bed spray granulation. Collect the alloy powder with a particle size of 12-75 The key parameters of the granulation process and detailed steps are as follows: first, the working chamber is vacuumized, the vacuum degree of the atomizing chamber reached $5\times10^{-3}$ Pa, and then high-purity argon gas was introduced to make the pressure in the chamber reach 0.06 MPa. The power of the plasma gun was at 200 kW, the rotation speed was 16000 r/min, and spherical powder was formed after cooling under the inert gas in the chamber and collected into the powder bin.
(3) Put the collected alloy powder into a vacuum drying box, where the vacuum pressure was about 120 MPa. Then the vacuum drying box was heated to 120° C. at a heating rate of 80° C./min and vacuum drying was performed after holding the temperature for 2 h. The titanium-based alloy powder obtained after drying is the biomedical β titanium alloy material of the present example, the alloy powder was put into a vacuum bag to be evacuated and stored for later use.

Example 4

The β titanium alloy materials prepared in Example 1, Comparative Example 1 and Comparative Example 2 were formed into parts by laser additive manufacturing. The specific manufacturing method includes the following steps:
Use Solidworks software to build a 3D model, then import it into Magics software to arrange the part and set the laser scanning sequence;
Pour the β titanium alloy material into a powder storage bin of the Selective Laser Melting (SLM) additive manufacturing system, and wait to obtain the part formed by laser selective melting;
The EOS M290 system was used to form and prepare alloy part samples from the β titanium alloy materials, which are metallographic test samples, tribocorrosion performance test samples and biological performance samples. The specific process parameters are: the laser spot was 100 μm, and the laser power was 100 W, the layer thickness was 30 μm, the scanning spacing was 100 μm, and the scanning speed was 500 mm/s.
It should be noted that the processes involved in the additive manufacturing system can also be specifically any one selected from the group consisting of electron beam additive manufacturing (EBAM), direct metal deposition (DMD), direct metal laser sintering (DMLS), laser near net shaping (LENS), laser metal forming (LMF), selective laser melting (SLM), selective laser sintering (SLS) and other techniques.

Figure 1:
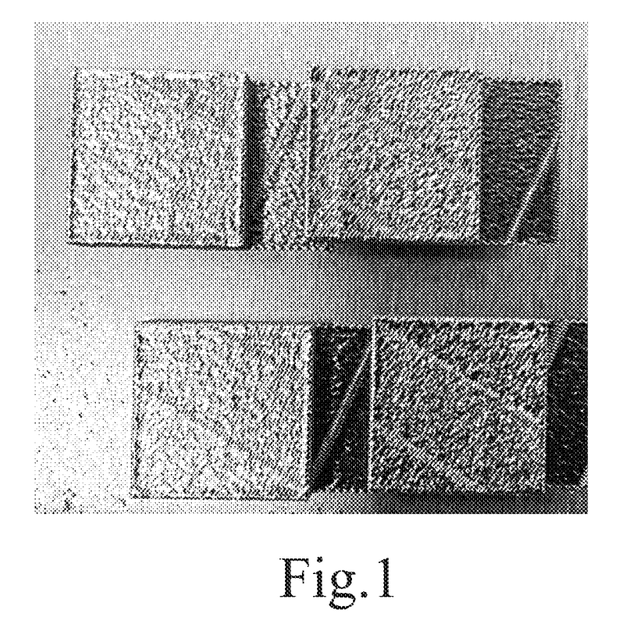
FIG. 1 is the morphological diagram of the SLM alloy sample prepared in Example 1 of the present disclosure.

The SLM alloy sample prepared in Example 1 is shown in FIG. 1, there are no cracks and holes on the surface, and it has excellent weldability and formability.

Figure 2A:
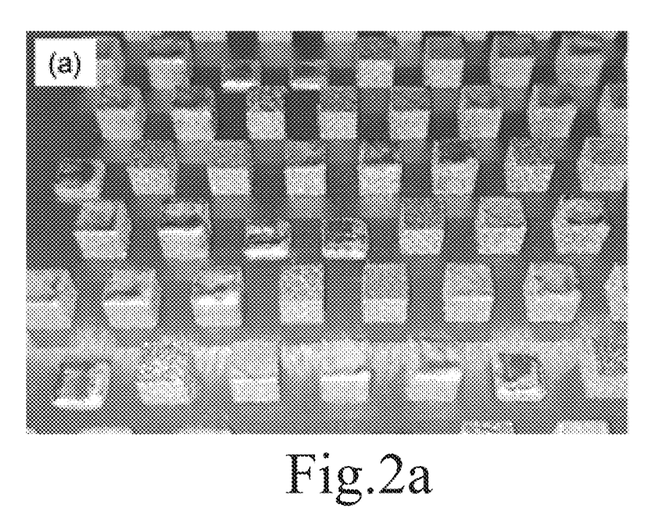
FIGS. 2a and 2b are the macroscopic morphology image (FIG. 2a) and the microscopic surface morphology (FIG. 2b) of the SLM alloy samples prepared in Comparative Examples 1 and 2.
Figure 2B:
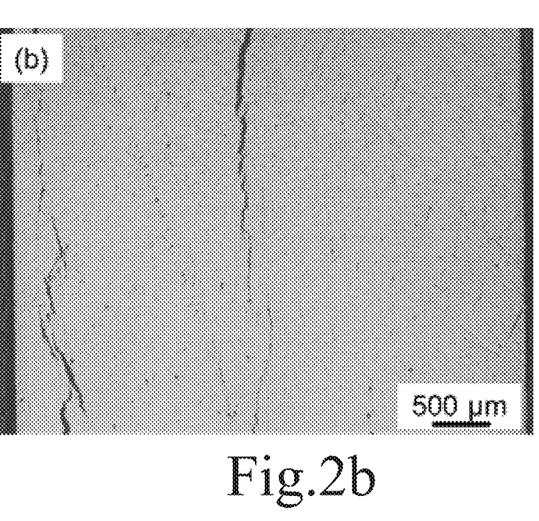

The SLM alloy samples prepared in Comparative Example 1 and Comparative Example 2 are shown in FIGS. 2a and 2b. There are pores and spalling on the macroscopic surface of the samples, and the weldability and formability are poor. Since the surface morphologies of SLM-formed samples in Examples 2 and 3 are similar, detailed distinction is not discussed again here.

Performance Test

The β titanium alloy samples prepared in Example 4 were subjected to material characterization, mechanical properties and biological properties tests.

Figure 3A:
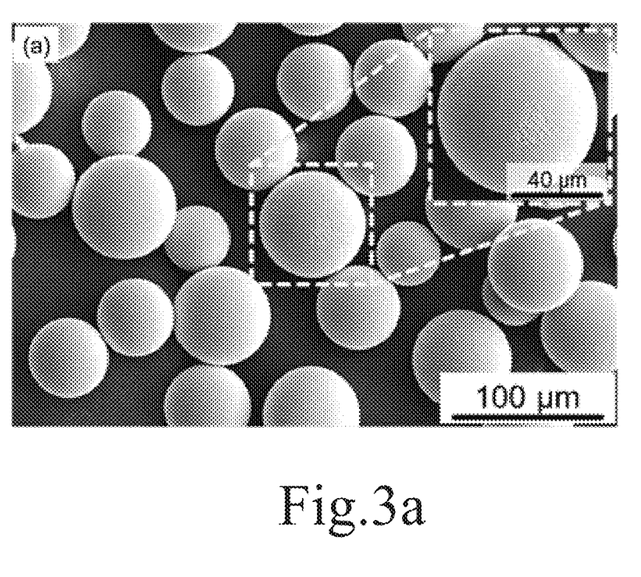
FIG. 3a is the SEM image of the β titanium alloy powder of the present disclosure.
Figure 3B:
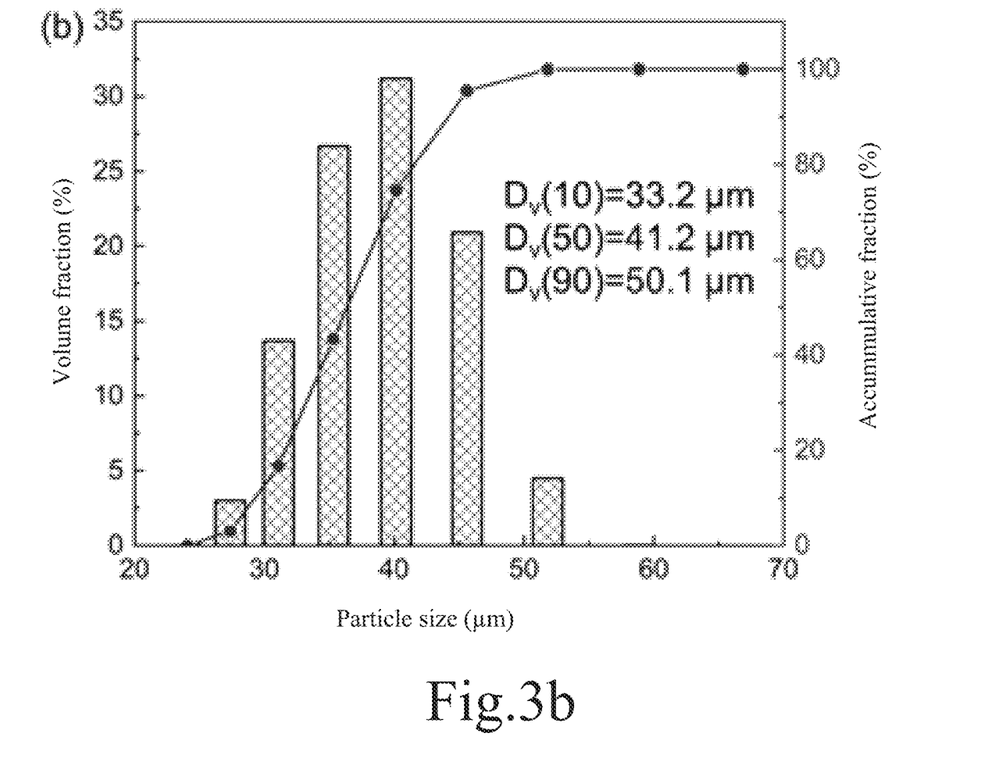
FIG. 3b is the particle size distribution diagram of the β titanium alloy powder.

It can be seen from FIG. 3a that the powder obtained in Example 1 is a β titanium alloy powder with extremely high sphericity, almost no satellite spheres, and has good fluidity; FIG. 3b shows the particle size distribution of the β titanium alloy measured in the example, where Dv(50)=41.2 µm, and it meets the requirement of powders commonly used in selective laser melting (SLM) in the present example.

Figure 4:
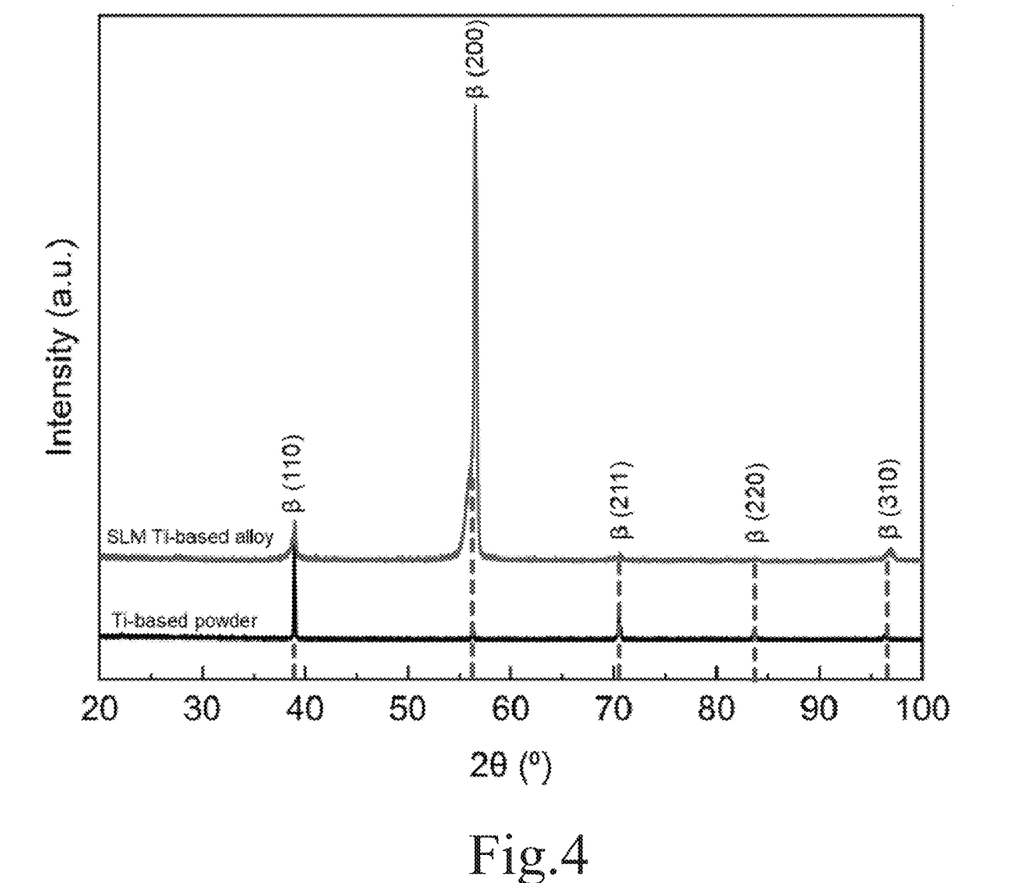
FIG. 4 is the XRD pattern of the β titanium alloy powder of the present disclosure and the β titanium alloy sample prepared by SLM.

It can be seen from FIG. 4 that only the peak position of the β-Ti phase can be detected whether it is the β titanium alloy powder of Example 1 or the β titanium alloy sample prepared by SLM in Example 4, indicating that the prepared β titanium alloy material achieved the expected effect.

Figure 5:
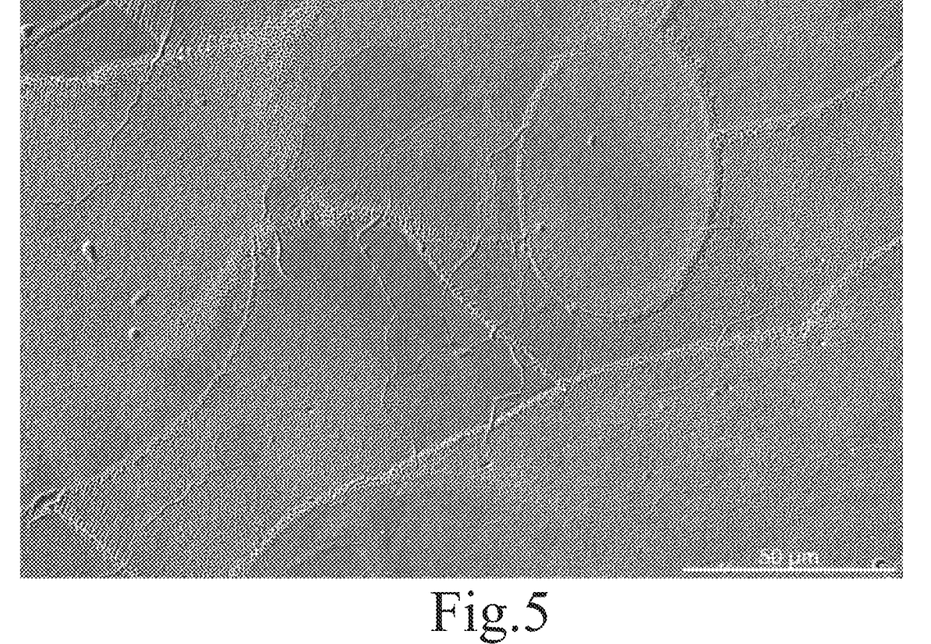
FIG. 5 is the SEM image of the β titanium alloy sample prepared by SLM.

Further, it can be seen from the SEM results of the SLM prepared β titanium alloy in FIG. 5 that the SLM prepared samples basically compose of completely dense and fine equiaxed grains, and there are only a small amount of columnar crystals existing at the junction of the melt channel. The average grain size is about 1.2 µm, indicating that the β titanium alloy material prepared by SLM has an extremely fine grain structure.

The average microhardness test was carried out on the β titanium alloy samples prepared in Example 4, and the test method was: use a microhardness tester (model Leitz Wetzlar, Germany) to measure the Vickers microhardness of the sample, under a load of 200 g and a dwell time of 25 s. Polish the surface of the test surface of the SLM samples to reach a roughness of less than 0.15 µm, measure the microhardness values at different positions on the surface of the SLM sample, and take an average value after 10 measurements. The average microhardness obtained by the testing was 356±6.2 $HV_{0.2}$.

The tribocorrosion performance test were carried out on the β titanium alloy sample prepared in Example 4. The test method was as follows: at room temperature (25° C.), a sliding ball-on-disk wear test was carried out on the sample using a CSEM tribometer. Before testing the tribocorrosion performance, the surface roughness (Ra) of all SLM samples was polished to less than 0.15 µm, silicon nitride ($Si_3N_4$) balls with a diameter of 4 mm were selected as countergrinding balls, and cleaned with ethanol before testing, 3.5 wt % NaCl physiological saline solution was loaded during the tribocorrosion performance test. The test conditions were as follows: the test load was 500 g, the rotational speed was 200 r/min, the friction distance was 188.5 m, and the friction diameter is 10 mm.

During the sliding test, the coefficient of friction (COF) is automatically recorded by the machine. After the test was completed, the wear surface of the sample was observed and analyzed with a scanning electron microscope, and the macro-morphology of the wear scar was measured with a three-dimensional surface profiler. The wear rate (w) of the sample is calculated by the following formula and an average value is calculated after three measurements:

$$\omega = \frac{2\pi r S}{W \times L}$$

where r is the radius of the wear track, in mm; S is the cross-sectional area of the wear track, in square millimeters; W is the test load, in N; L is the sliding distance, in m. The measured average friction coefficient was 0.62, and the average wear amount was $2.38 \pm 0.25 \times 10^{-4}$ mm3/(N·m).

The in vitro cytotoxic effect of the β titanium alloy samples prepared in Example 4 was analyzed using rat bone marrow mesenchymal stem cells (rBMSCs), which met the international standard ISO 10993-5. A Liquid extract of the sample (37° C., containing 10% FBS (v/v), 3 $cm^2$/ml in α-MEM) was prepared and filter sterilized prior to use in the cytotoxicity assay carried out with a cell counting kit-8 (CCK-8). BMSCs were seeded in 96-well plates (Nest, USA) at a density of $1 \times 10^4$ cells per well for one day, and the culture medium was replaced with medical grade polyethylene (negative control, no cytotoxicity), α-MEM (positive control, for providing reproducible cytotoxic response) containing 10% FBS (v/v) and 10% dimethyl sulfoxide (DMSO), and the liquid extract of the β titanium alloy samples from each group (100 µL/well), for 1, 3 and 5 days. Subsequently, 10 µL of CCK-8 solution was added to each well of the plate, and the plate was incubated in light for two hours. Measure the absorbance at 450 nm, and the measured values from the negative control wells were averaged and taken as 100% cell viability. All other values were then averaged relative to their group and compared to the negative control group. The measured results show that the cell absorbance (OD value) of the β titanium alloy samples prepared by SLM after 1 day, 3 days and 5 days were 1.275, 1.351 and 1.333, respectively, which were slightly superior to those of Ti-6Al-4V ELI at 0.04, 0.6 and 1.6. Meanwhile, the cytotoxicity experiment performed on the Example 1 sample showed that the number of viable cells (stained viable cells area per unit area) after 24 hours was 20.2%, much higher than that of Ti-6Al-4V ELI (11.3%), indicating that the prepared β titanium alloy sample has very low cytotoxicity and good cytocompatibility.

Figure 6A:
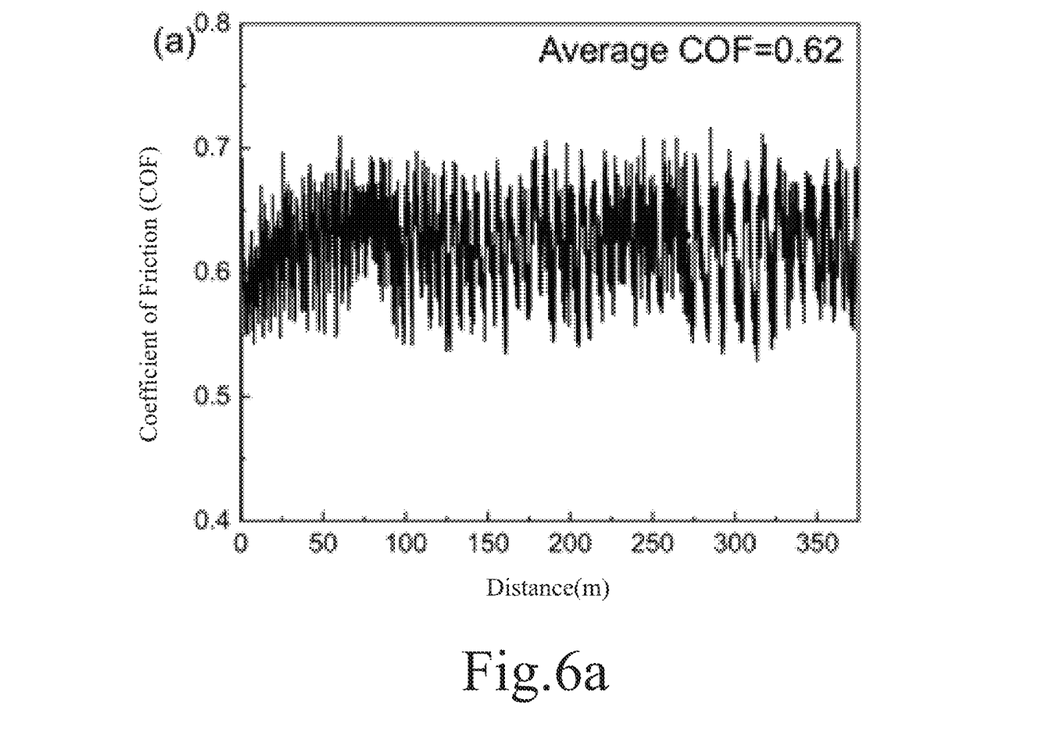
FIGS. 6a and 6b show the tribocorrosion performance of the β titanium alloy samples prepared by SLM in 3.5 wt % NaCl solution: COF distance curve (FIG. 6a); SEM image of the wear surface (FIG. 6b).
Figure 6B:
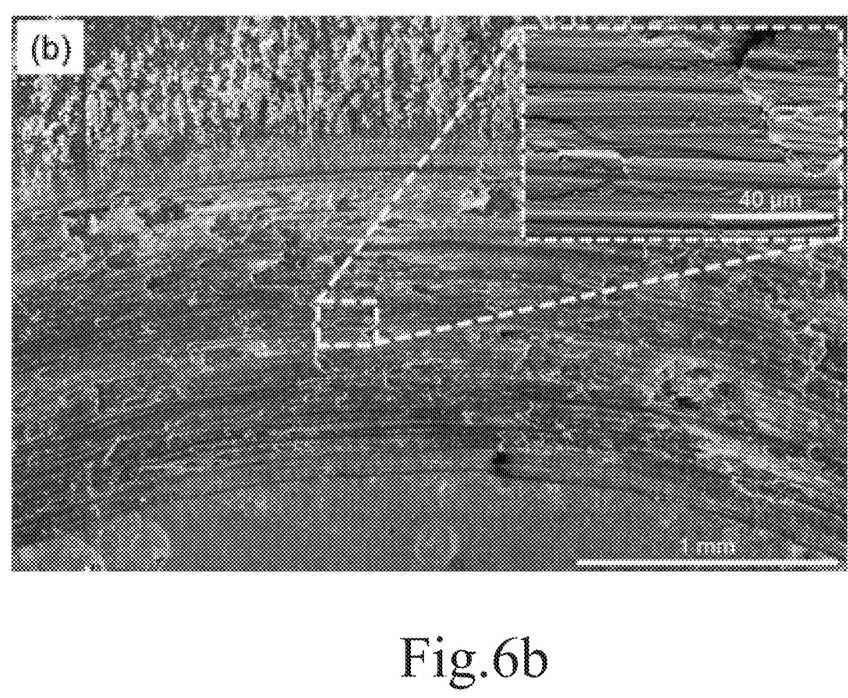

FIG. 5, FIG. 6a and FIG. 6b and the test results of the above-mentioned material properties show that the currently invented β titanium alloy powder itself has excellent fluidity, high purity and weldability, and the β titanium alloy materials prepared by SLM process have strong hardness, and the biological compatibility and tribocorrosion resistance both have good performance. It indicates that the β titanium alloy material invented by the technical solution of the present disclosure is a new type of non-toxic, low-elastic and tribocorrosion resistant biomedical β titanium alloy that can reach the biomedical level and is suitable for metal additive manufacturing.

Finally, it should be noted that the above embodiments are only used to illustrate the technical solutions of the present invention and not to limit the protection scope of the present invention. Although the present invention is described in detail with reference to the preferred embodiments, those of ordinary skill in the art should understand that, the technical solutions of the present invention may be modified or equivalently replaced without departing from the spirit and scope of the technical solutions of the present invention.

The invention claimed is:

1. A β titanium alloy material prepared from a biomedical β titanium alloy powder, wherein the β titanium alloy material composes of equiaxed crystals and columnar crystals existing at a junction of melt channels, and has an average grain size of 1.2 μm and an average microhardness of 356±6.2 $HV_{0.2}$;

the β titanium alloy powder comprises the following components by mass percentage: Mo: 11.25%; Fe: 1.75%; Zr: 5.82%; Ta: 0.21%; the balance is Ti and inevitable impurities; the biomedical β titanium alloy powder only has a β-Ti phase and a Dv(50) of 41.2 μm;

the method for preparing the biomedical β titanium alloy powder comprises the following steps:

(1) Mixing Mo, Fe, Zr, Ta and Ti according to the mass percentage, smelting and forging into a rod;

(2) Fabricating an alloy powder from the rod obtained in step (1) by a plasma rotating electrode process, and collecting the alloy powder with a particle size of 12-75 μm;

(3) Vacuum drying the alloy powder collected in step (2) to obtain the β titanium alloy;

wherein, the plasma rotating electrode process in step (2) is carried out by heating the rod in step (1) to 1500-1750° C. in a vacuum environment, and smelting for 60-80 minutes to obtain a molten alloy, introducing high-purity argon 99.999 vol. % for fluidized bed spray granulation.

2. The β titanium alloy material of claim 1, wherein the rod in step (1) has a diameter of 15-30 mm, and a length of 10-150 mm.

3. The β titanium alloy material of claim 1, wherein the rod in step (1) has a diameter of 15-20 mm, and a length of 20-30 mm.

4. The β titanium alloy material of claim 1, wherein the alloy powder in step (2) is spherical, and the particle size of the collected alloy powder is 35-50 μm.

5. The β titanium alloy material of claim 1, wherein, in step (3), the vacuum drying is carried out at 120-200° C., and under a pressure of 100-200 MPa.

* * * * *